United States Patent [19]
Vichard

[11] Patent Number: 6,080,159
[45] Date of Patent: Jun. 27, 2000

[54] ASCENDING CENTROMEDULLARY THIGH BONE PIN WITH MECHANICAL CLAMPING OF ITS TWO ENDS

[75] Inventor: Philippe Vichard, Besancon, France

[73] Assignee: Sulzer Orthopedics Ltd., Baar, Switzerland

[21] Appl. No.: 08/913,903

[22] PCT Filed: Jul. 16, 1996

[86] PCT No.: PCT/FR96/01097

§ 371 Date: Oct. 23, 1998

§ 102(e) Date: Oct. 23, 1998

[87] PCT Pub. No.: WO98/02104

PCT Pub. Date: Jan. 22, 1998

[51] Int. Cl.[7] ..................................... A61B 17/72
[52] U.S. Cl. ................................. 606/64; 606/98
[58] Field of Search .................. 606/60, 62, 63, 606/64, 96, 97, 98, 99, 104

[56] References Cited

U.S. PATENT DOCUMENTS

| | | | |
|---|---|---|---|
| 2,821,979 | 2/1958 | Cameron | 606/64 |
| 4,622,959 | 11/1986 | Marcus | 606/64 |
| 5,179,915 | 1/1993 | Cohen et al. | 606/62 |
| 5,248,313 | 9/1993 | Greene et al. | 606/62 |

FOREIGN PATENT DOCUMENTS

| | | |
|---|---|---|
| 2668360 | 4/1992 | France . |
| 2690330 | 10/1993 | France . |
| WO 92/01422 | 2/1992 | WIPO . |

*Primary Examiner*—Michael Buiz
*Assistant Examiner*—David O. Reip
*Attorney, Agent, or Firm*—Collard & Roe, P.C.

[57] ABSTRACT

An interlocking intramedullary nail system has a nail having an upper extremity, a lower extremity and transverse locking ducts in the upper and lower extremity, a plurality of fixation bone screws adapted to be received by the locking ducts, an attachable lower guide at the lower extremity of the nail, a perforator-guide detachably-fixed to the upper extremity of the nail, and an attachable upper guide at the upper part of the perforator-guide for precisely meeting the locking ducts in the upper extremity of the nail. A method of interlocking an intramedullary nail using this system attaches the perforator-guide to the nail, perforates a bone along its medullary canal with the nail and the perforator-guide until the upper part of the perforator-guide has left the bone, and attaches the upper guide to the upper part of the perforator-guide. Holes are drilled into the bone using the locking ducts of the upper guide and bone screws inserted into the upper extremity locking ducts to secure the nail to the bone. The upper guide and the perforator-guide are detached, and the lower guide is attached to the lower extremity of the nail. Additional holes are drilled into the bone using the locking ducts of the lower guide and bone screws inserted into the lower extremity locking ducts to secure the nail to the bone. The lower guide is then detached from the nail.

9 Claims, 8 Drawing Sheets

ASCENDING CENTROMEDULLARY THIGH BONE PIN WITH MECHANICAL CLAMPING OF ITS TWO ENDS

BACKGROUND OF THE INVENTION

1. Field of the Invention

The invention relates to a so-called ascending centro-medullary nail (i.e., the point of its introduction is located in the knee joint), which is fixated in the distal epiphysis of the femur by a mechanical method, and fixated at the level of the proximal metaphysis of the femur by mechanical means as well, as described further below.

2. The Prior Art

Said nail is intended for generally treating fractures located at the ⅓ distal level of the femur, specifically metaphyseal fractures;

fractures in the metaphyseal and diaphyseal stages; and certain epiphyseal fractures.

In the most favorable case, centro-medullary pinning—whether fixated or not—interlocks at least two fragments of equal length (1). If the or one of the lines of fracture extends close to an epiphysis, the best mechanical solution is to introduce the nail within the proximity or the epiphysis involved (2). On the other hand, the nail, due to its long centro-medullary extension in the largest of the fragments, automatically orientates the shorter of the two fragments.

Taking into account the above procedures, surgeons heretofore made use or the trochanteric method depending on the location of the line of fracture of the femur. Due to the nature of this approach, which is not very satisfactory, surgeons often fail with the pinning for securing the plates bent most often (3) in support of the epiphysis; in fact, conventional pinning, even if interlocked, is exposed to the following risks:

(1) The mechanical advantages of catheterizing first the shortest fragment of the femur are obvious.

(2) The nail may end in one of the condyles, which interferes with the reduction and may lead to severe callosity.

(3) The epiphyseal corner lines may become enlarged and the more or less identified fragments may be mobilized.

(4) The distal fixation is radioscopic, which is a source causing problems and irritation for medical and paramedical personnel.

On the other hand, resorting to the plate, which is viewed as being indispensable, is not an ideal solution. In fact, it acts as an intervention with the open roof extensively, and as such is a source of bleeding due to postoperative infection and difficult healing.

SUMMARY OF THE INVENTION

The objective of the present innovation is to permit a centro-medullary fixation interlocked in the closed center without the drawbacks of the conventional pinning specified above, but with the following advantages:

(a) Mechanical fixation at the two extremities of the nail;

(b) Utilization of a limited number of nails and of a simple auxiliary material, providing the surgeon with
one single nail length;
two diameters; and
nails interchangeable between right and left.

BRIEF DESCRIPTION OF THE DRAWINGS

The present invention is explained by the attached drawings, in which.

DETAILED DESCRIPTION OF PREFERRED EMBODIMENTS

MATERIAL (A) NAIL (4,5)

Figure 1:
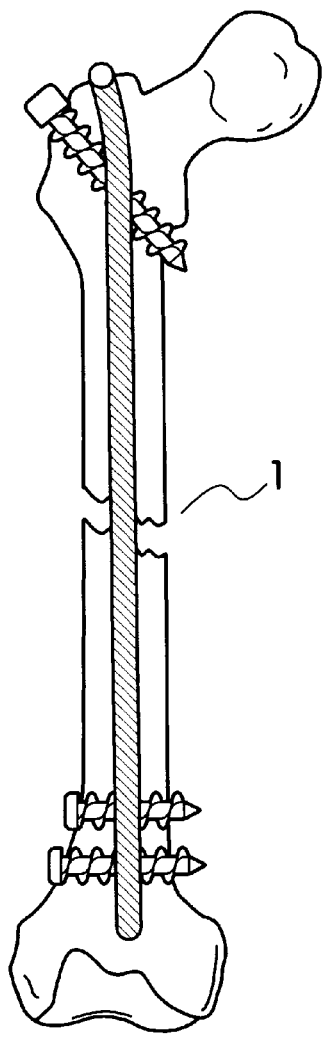
FIG. 1 shows a conventional centro-medullary pinning of the femur, interlocking two diaphyseal fragments of equal length.
Figure 2:
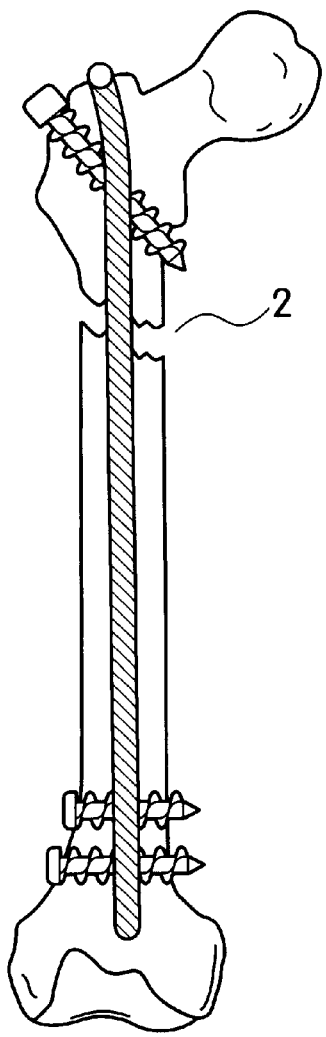
FIG. 2 shows a conventional centro-medullary pinning interlocking two fragments of unequal length. The assembly is satisfactory, as the line of fracture is close to the trochanteric point of introduction of the nail.
Figure 3:
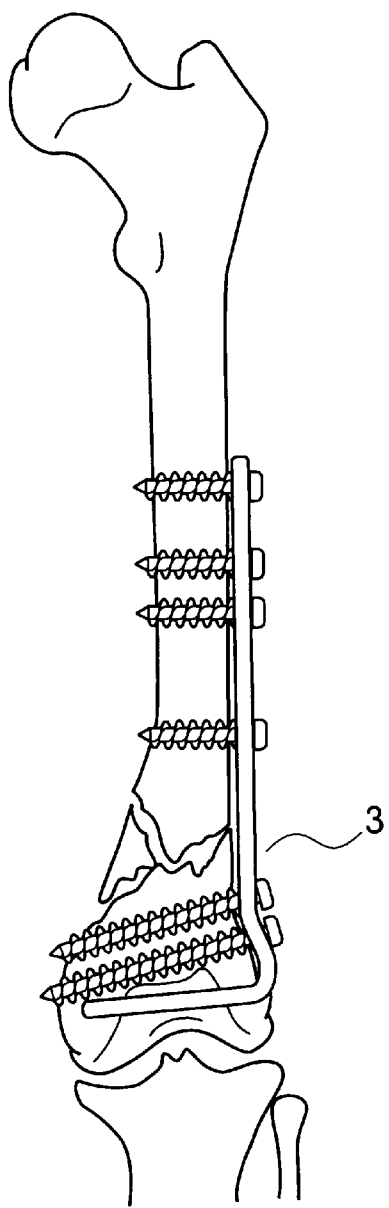
FIG. 3 shows an angled plate interlocking the two main fragments of the femoral fracture in the distal ⅓rd part of the femur. For various reasons outlined in the following, introduction of a centro-medullary nail at a trochanteric point is not satisfactory.
Figure 4:
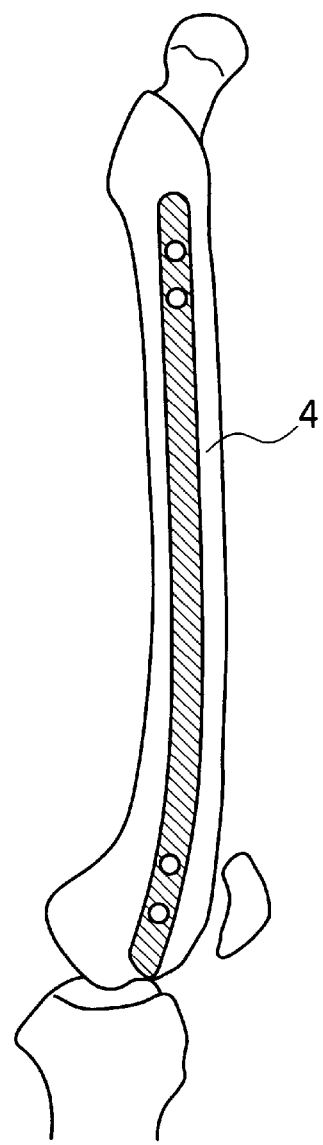
FIG. 4 shows the profile of an ascending centro-medullary nail, the latter being curved in the sagittal plane.
Figure 5:
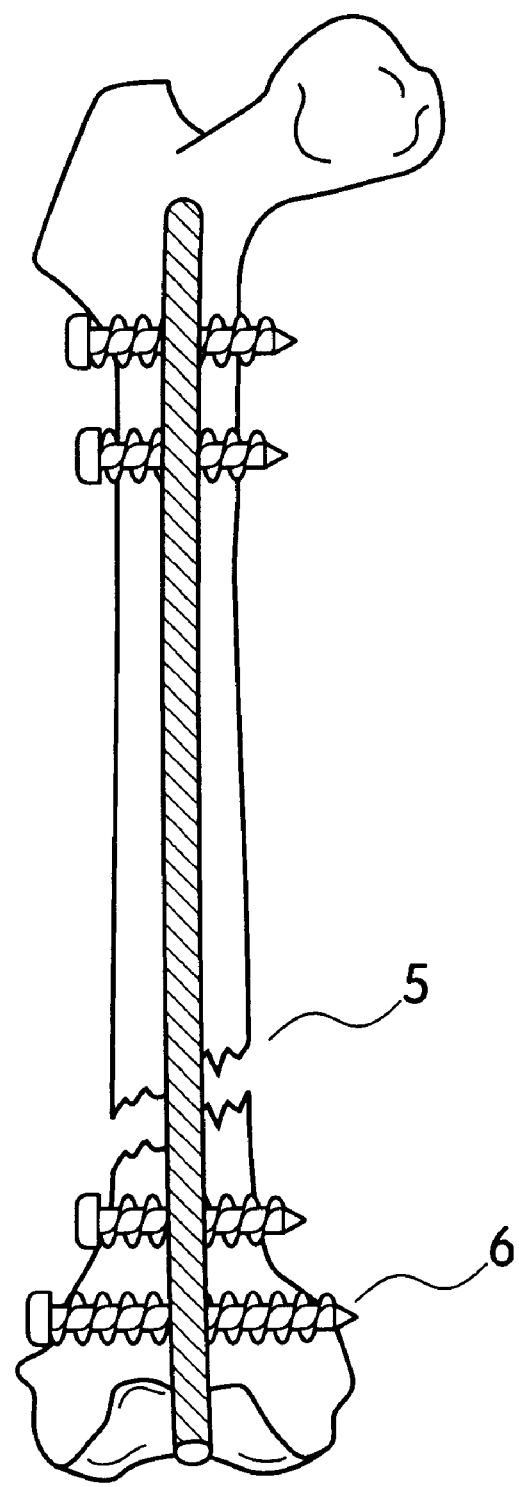
FIG. 5 shows a front view of the ascending nail.
Figure 6:
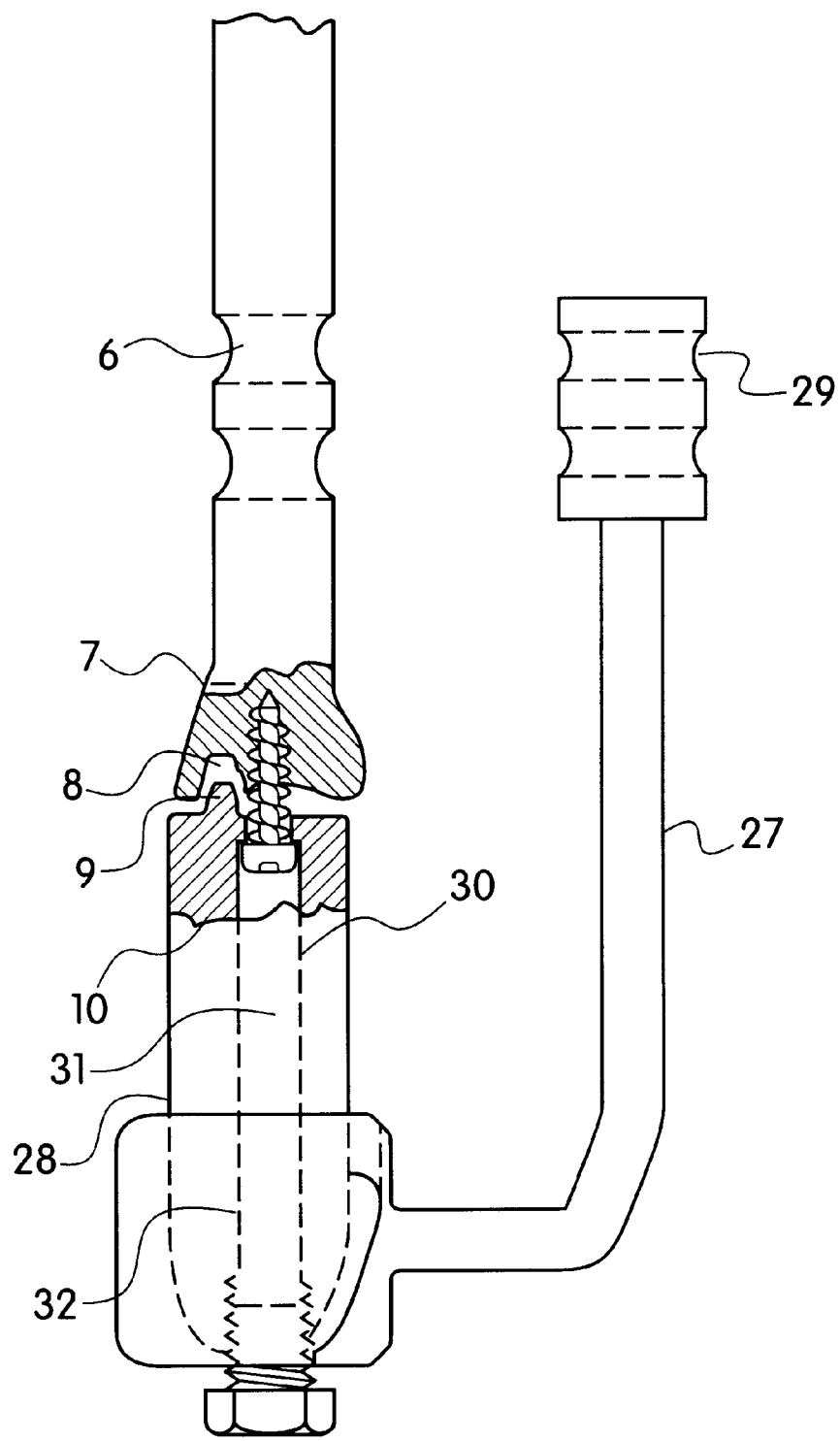
FIG. 6 shows the assembled fixation comprised of the ascending nail, adapter and universal guide.
Figure 7A:
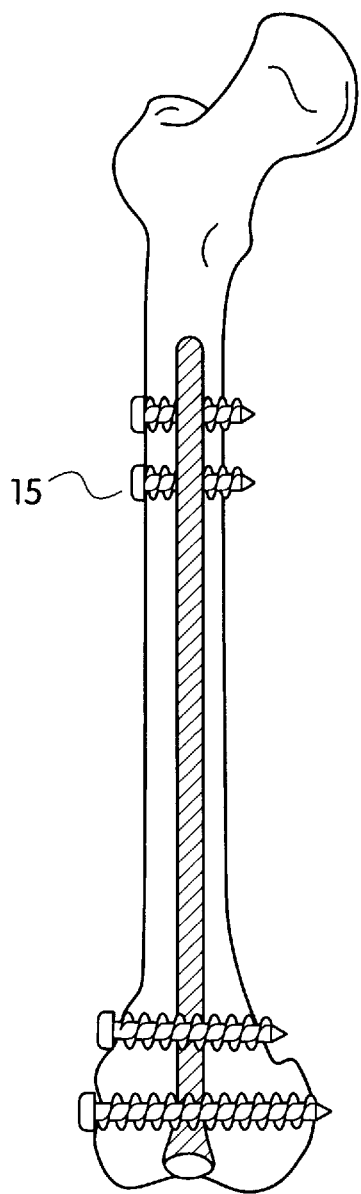
FIG. 7 show the variable position of the subtrochanteric fixation adaptable to the length of the femur when the use of only a very limited number of nails is deemed desirable.
Figure 7B:
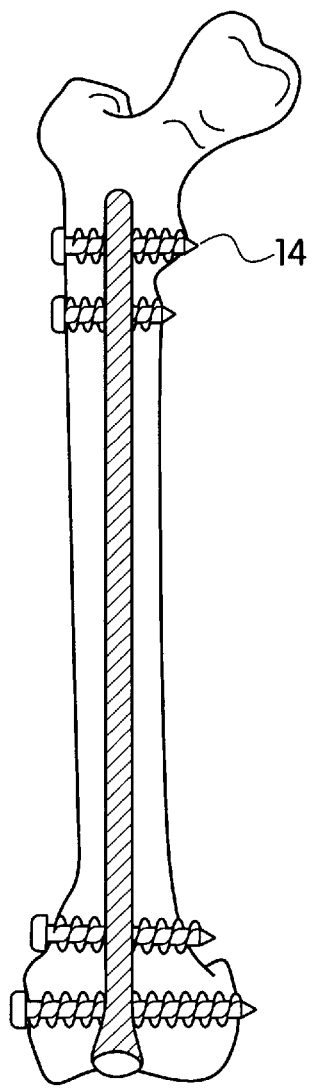
Figure 8A:
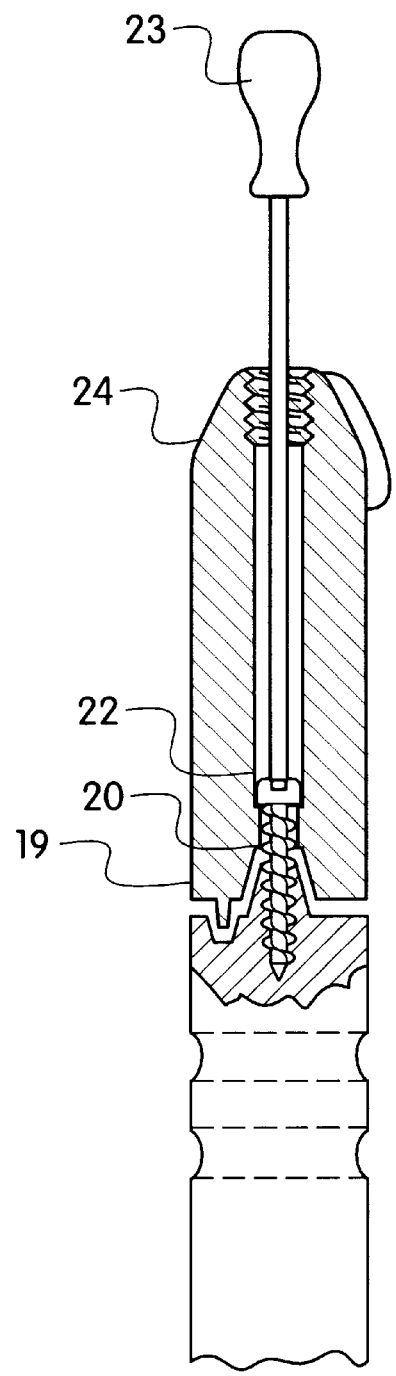
FIG. 8 show the articulation of the perforator-guide and nail.
Figure 8B:
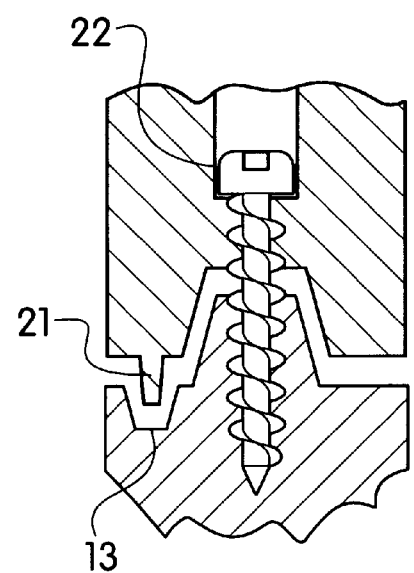
Figure 9:
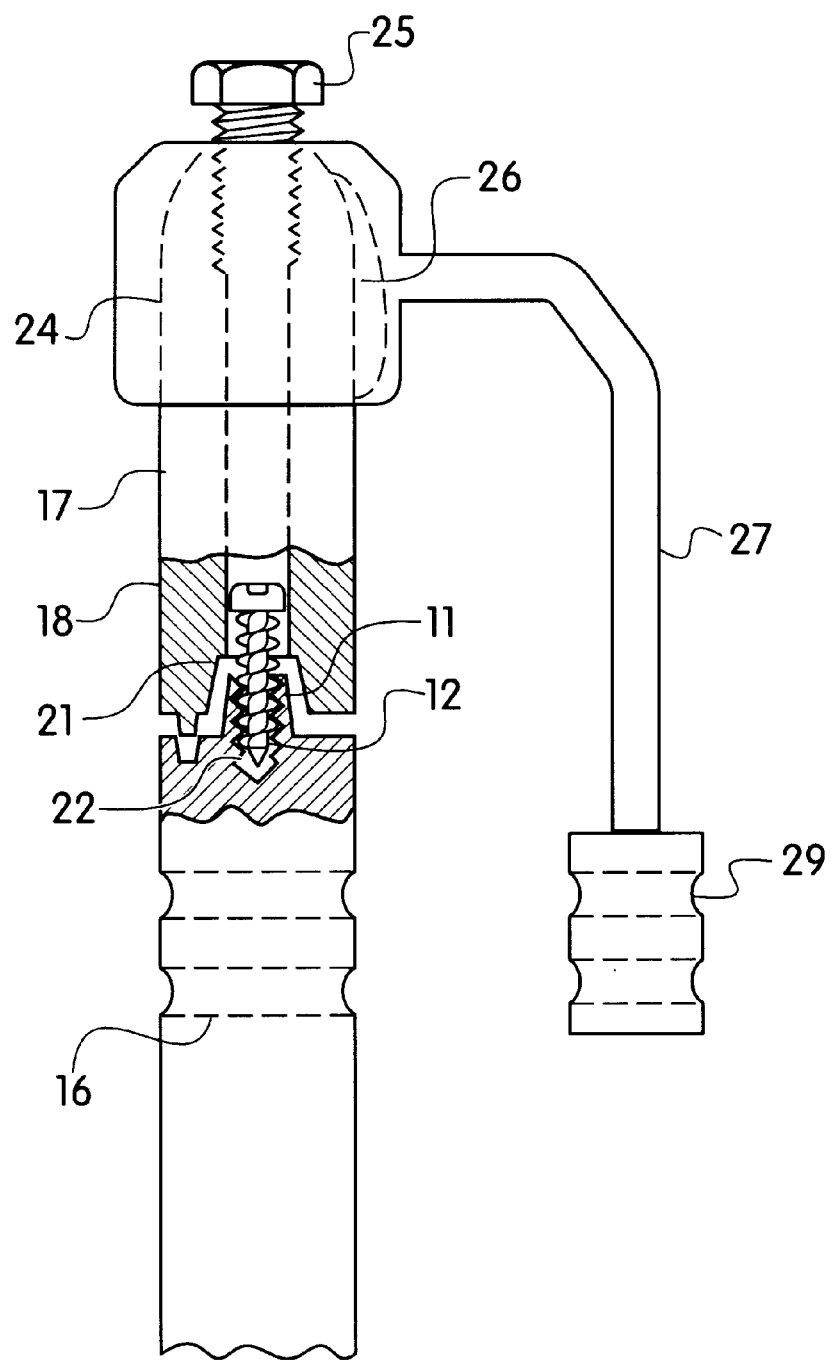
FIG. 9 shows the assembly of the fixation comprised of nail, perforator-guide and universal guide.
Figure 10:
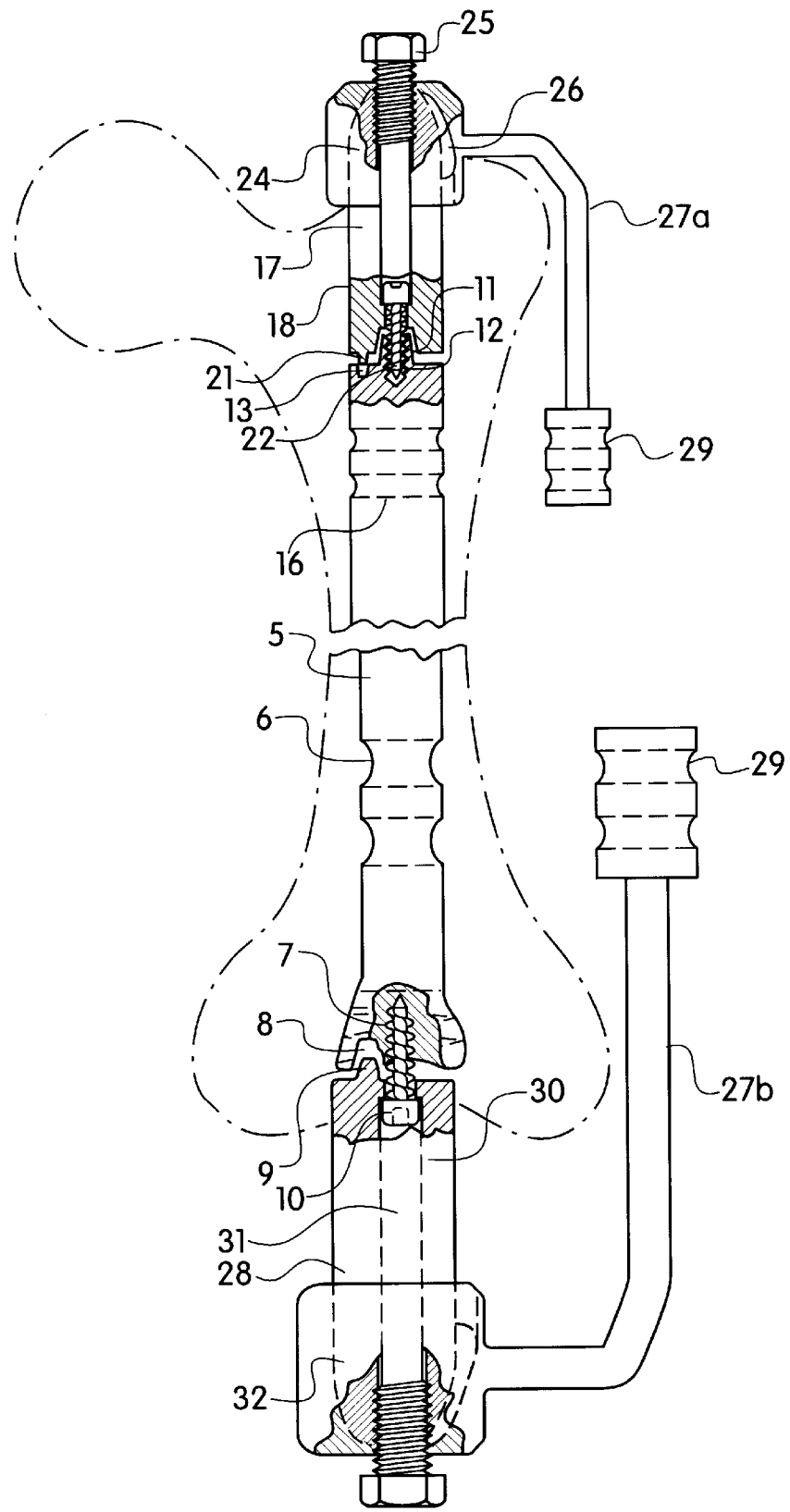
FIG. 10 shows a complete assembly of the interlocking intramedullary nail system of the present invention.

The nail (4,5) is a fully cylindrical pin adapted to the shape of the medullary canal in that it is curved in the sagittal plane (FIG. 4). The nail is pierced by two locking apertures or ducts (6) extending in the frontal direction in parallel very close to its lower extremity. The term "extremity" is used because intervention is finally located in the knee joint.

At the level of the lower extremity of the nail, a female thread (7) and a small notch (8) permit screwing a group of pieces approximately in the form of a "U" into the male element (9) for securing such pieces in the female thread of the nail. A screw (10) then interlocks the nail and the auxiliary material.

The upper extremity or end (11) of the nail (the term "extremity" or "end" is used as intervention is finally located in the proximal metaphysis of the femur) is formed by a cylinder having a base with a diameter slightly smaller than the one of the center part of the nail. Said cylinder with reduced dimensions is hollow. The hollow zone disposed in the upper part has a cylindrical shape and is threaded (12) for receiving a screw. At the base of the cylinder with the reduced dimensions, the nail itself supports a female notch (13) designed for hinging with the male projection (21) of the perforator-guide (see further below).

The nail has a length usable for all femurs. Fixation can be realized at the level of the minor trochanter [for the shortest femurs (14)] up to the level of the proximal ⅓rd part of the femur [for the longest femurs (15)]. The nail has two additional locking ducts (16) extending in the frontal direction very close to the body of the cone mentioned above.

(B) AUXILIARY MATERIALS (1) Perforator-Guide (17)

The perforator-guide has a tapering cylindrical shape tapering from the bottom to the top. Its largest diameter is equal to the one of the nail at its top extremity (excluding the cylinder intended for articulating with the perforator-guide).

The perforator-guide is comprised of three parts:

(a) A center part (18) spaced over its entire length from the longest cylindrical, expanse by an interior cylinder.

(b) A lower part (19), which is also hollow and has a female cylinder (20) with reduced dimensions extending therethrough, such cylinder being adapted for articulating with the male projection of the upper extremity of the nail. A male projection (21) articulates with the female notch (13) of the upper extremity of the nail.

A screw (22) is secured with the help of a long screwdriver (23). The head of the screw has a diameter larger than the one of the top of the small female cylinder.

(c) An upper part (24) The different diameters of the perforator-guide decrease progressively, so that the nail/perforator-guide assembly has a form approximately similar to a truncated cone.

Said top part is hollow as well and the interior cavity represents a cylinder having the same diameter as the lower part.

However, a thread extends through the face of said cylinder, and a screw (25) admitted with the help of said thread closes the central canal of the perforator-guide, or locks the latter with the universal guide of the fixation (such guide is described further below). A sharp longitudinal elevation extends across the outer surface of said top part, reaching the upper extremity of the perforator and articulating with a female grooving of the universal guide of the fixation (see description further below).

(2) Universal Guide of the Fixation (27)

This guide is referred to as a universal element because it serves for securing both the lower and upper extremities of the fixation system with the help of an adapter (28), which, for the lower fixation, replaces the perforator-guide used for the upper fixation.

The universal guide of the fixation is a square arrangement, articulating with the perforator-guide or adapter and providing the assembly with the overall configuration of a "U". Longitudinally, a four-angled section is disposed in the square.

It is pierced by two parallel cylindrical looking ducts (29) extending in the frontal direction.

The position of said two cylindrical ducts is selected in a way such that a bit introduced percutaneously smoothly reaches the orifices of the fixation in the lower and upper extremities of the nail. Likewise, the grooves, projections (26) or elevations (male or female, respectively) of the nail and perforator-guide (17), adapter and fixation locks are arranged in such a way that the present mechanical design is made possible.

(3) Adapter (28)

The adapter has an external shape analogous to the one of the perforator-guide. Its larger diameter is designed in a way such that it is adapted to the lower extremity of the nail with the help of the female cylindrical cavity in the latter, such cavity being threaded for receiving a screw. It consists of three parts: a base, a body and a top part.

Base (30) of the adapter (its extremity, too, is fixed on the nail in the knee joint) is notched and supports a male element (9) adapted to the female notch (8), and the lower extremity of the nail. A centro-medullary screw interlocks the nail and adapter; male element and female notch are precision-articulated. Furthermore, a cylindrical cavity extends through the interior of said base, interrupted at its articulating extremity—the nail—by a diaphragm traversed by the screw adapted to the thread of the nail.

The center part (31) of the adapter is analogous to the one of the perforator-guide.

The top part (32) of the adapter is in every way analogous to the one of the perforator-guide in that it articulates with the universal guide of the fixation system.

FIXATION METHOD

The disorder is dorsal decubitus on a normal table; the proximal fragment of the femur is raised with a transversal bar. For very distal fractures, a pneumatic tourniquet can be used for preventive hemostasis.

The field of operation comprises all lower members, which can be manipulated by an assistant. The operative field includes the hip region. The reduction of the fracture and the progression of the nail are visualized and observed with the help of a luminance-amplification device which, however, is not required for any other purpose.

Longitudinal traction realized by an assistant may be facilitated by a transtibial pin.

(1) Marking of the Entry Opening for the Nail in the Joint

The joint is flexed by the assistant. A short internal parapatellar incision permits marking of the entry opening with the index finger, such opening being located in the intercondylar indentation just behind the cartilage in front of the inlets of crossed ligaments. A square-tipped lance introduced with the palm of the hand together with the forefinger for marking the site opens the medullary canal.

The opening is gradually enlarged with the help of square-tipped lances with crescent-shaped edges.

The perforator-guide is secured on the nail and the assembly is pushed into the medullary canal without prior drilling. However, prior drilling may be carried out for pining under certain special circumstances (medullary canal altered by lesions or previous interventions).

(2) Nail and Perforator-guide Assembly:

It is pushed into the medullary canal and reaches the "constricted passage" (narrow zone in diabolo of medullary canal, center ⅓rd). After said zone has been cleared (verification with help of luminance amplifier), the focus of the fracture is reduced in the frontal and sagittal planes. The entry point and at least two points of the medullary canal are then aligned.

However, the surgeon needs to pay attention to axial rotation of the distal femur, as well as to possible telescoping of the principal fragments. Finally, excessively forceful manipulation of the epiphysis prior to lower fixation may ensue displacement of said epiphysis in the frontal and sagittal planes due to basculation of said epiphysis around the entry opening of the nail, and eventually result in a highly comminuted fracture.

The assembly of nail and perforator, which has a length exceeding the one of all femur variations, progresses and perforates the crown of the trochanter. This is the site where the lower fixation of the femur is put into place with the help of the adapter/universal guide assembly of the fixation system.

It is deemed good practice if, as mentioned above, basculation of the epiphysis around the entry opening of the nail can be avoided. However, such lower fixation can be realized also later.

The lower fixation comprises the following steps:

(a) The base of the adapter is screwed to the nail with the help of a long screwdriver extending through the internal duct of the adapter for screwing the latter to the nail.

(b) The universal guide is screwed into place.

(c) Correct fixation, including insertion of the bit in the fixation ducts of the universal guide, permitting bicortical trephination of the femur, such trephination being preceded by a cutaneous incision and preparation of the bicortical trephination with the help of an adapted, square-tipped instrument;

measuring the length of the screw; and mounting of the two fixation screws.

After penetrating the crest of the trochanter, the perforator-guide driven by the nail forces back the muscles (it is called a perforator-guide because of said function) and causes the skin to be jutted out as far as permitted by adduction of the hip with the help of the assistant. An incision is made in the skin of the hip and the perforator-guide is visible.

It subsequently suffices to adapt the universal guide to the perforator and to proceed with the upper fixation under the same conditions as with the lower fixation.

The universal fixation guide and the perforator-guide are removed by reversing the steps carried out for putting said elements into place.

Restoration of points separated in the skin of the hip. Closure of synovialo-aponeurotic level and cutaneous level of the knee.

POSTOPERATIVE CARE

The knee and the hip can be mobilized immediately.

LEGEND OF DIAGRAMS

1. Classic centromedullary pinning, joining or interlocking two disphyseal fragments of equal length.
2. Classic centromedullary pinning, with trochanteric point of insertion of the nail. This type of nailing is satisfactory, mechanically speaking, if the proximal fragment is shorter than the distal one.
3. Angled (bent) plate joining the two main fragments when the femoral fracture is located in the ⅓ distal position on the bone.
4. Centromedullary nail rising curved in the sagittal plane.
5. Nail rising from the face.
6. The two locking apertures at the lower end of the rising centromedullary nail.
7. Thread located at the level of the lower hollow end of the rising nail, permitting the adapter and the nail to be joined.
8. Female notch in lower end of nail.
9. Male element of adapter.
10. Screw joining the adapter and the lower end of the nail.
11. Upper end of nail and its hollow cylinder.
12. Thread in walls of hollow cylinder. The interior of the cylinder is hollow. The cavity is cylindrical. The walls are covered by a thread.
13. Female notch of nail located in the center of the nail in the truncated-cone junction.
14. For short femurs, the upper end of the nail is locked or fixed near the trochanteric mass.
15. For long femurs, the upper end of the nail is locked much farther from the trochanteric mass.
16. Locking ducts in upper end of nail.
17. Perforator-guide.
18. Center part of perforator-guide.
19. Lower part of perforator-guide.
20. Female cylinder jointed with male cylinder of nail.
21. Male projection jointed with female part of the upper end of the nail.
22. Screw connecting the two male and female channels.
23. Long-shank screwdriver for mounting the screw joining the nail and the perforator-guide.
24. Upper part of perforator-guide.
25. Screw inserted in the thread covering the hollow cylinder located at the upper end of the perforator and extending the hollow cylinder in the middle section.
26. Longitudinally crest jointed with the female crest of the universal guide of the locking system.
27. Universal guide of locking system.
28. Adapter.
29. Locking channels or ducts of universal guide.
30. Adapter base.
31. Center part of adapter.
32. Summit of adapter.

I claim:

1. An interlocking intramedullary nail system comprising:

(a) a nail adapted to be introduced by way of an intercondyler opening and to fit the shape of a medullary canal of a bone, said nail having an upper extremity, a lower extremity and transverse locking ducts in the upper extremity and the lower extremity;

(b) a plurality of fixation bone screws adapted to be received by the locking ducts;

(c) an attachable lower guide at the lower extremity of the nail for precisely meeting the locking ducts in the lower extremity;

(d) a perforator-guide detachably-fixed to the upper extremity of the nail for perforating the bone, said perforator-guide having an upper part and a lower part, said perforator-guide being detachable from the nail when the upper part protrudes from the perforated bone; and (e) an attachable upper guide at the upper part of the perforator-guide for precisely meeting the locking ducts in the upper extremity of the nail.

2. An interlocking intramedullary nail system according to claim 1 wherein the nail, the lower guide and the upper guide are sized for a femur bone.

3. An interlocking intramedullary nail system according to claim 1 wherein the upper extremity of the nail and the perforator-guide have the same radial dimensions.

4. An interlocking intramedullary nail system according to claim 1 further comprising an adapter detachably mounted between the lower extremity of the nail and the lower guide.

5. An interlocking intramedullary nail system according to claim 4 wherein the upper guide comprises a plurality of locking ducts and the adapter includes (a) a base coupled to the lower extremity of the nail;

(b) a hollow center part; and (c) a summit coupled to the upper guide and dimensioned such that the locking ducts in the lower extremity of the nail are precisely met by the locking ducts of the upper guide.

6. An interlocking intramedullary nail system according to claim 5 wherein the adapter is hollow, said system further comprising (a) a screw;

(b) a plurality of coupling elements for attaching the adapter in a selected position whereby the screw is inserted through the hollow adapter.

7. An interlocking intramedullary nail system according to claim 1 further comprising (a) a cylindrical projection at the upper extremity of the nail comprising a thread inside said cylindrical projection;

(b) a corresponding counter part to the cylindrical projection in the lower part of the perforator-guide;

(c) a female notch at the upper extremity of the nail;

(d) a male projection at the lower part of the perforator-guide joined to the female notch; and (e) a screw insertable through the perforator-guide and held by the thread inside said cylindrical projection for clamping the perforator-guide to the cylindrical projection.

8. A method of interlocking an intramedullary nail using an interlocking system comprising a nail having an upper extremity, a lower extremity and transverse locking ducts in the upper and lower extremity, a plurality of fixation bone screws adapted to be received by the locking ducts, an attachable lower guide at the lower extremity of the nail, said lower guide comprising a plurality of locking ducts, a perforator-guide detachably-fixed to the upper extremity of the nail, an attachable upper guide at the upper part of the perforator-guide for precisely meeting the locking ducts in the upper extremity of the nail, said upper guide comprising a plurality of locking ducts, the method comprising the steps of:

(a) attaching the perforator-guide to the nail;

(b) perforating a bone along its medullary canal with the nail and the perforator-guide until the upper part of the perforator-guide has left the bone;

(c) attaching the upper guide to the upper part of the perforator-guide;

(d) drilling holes into the bone using the locking ducts of the upper guide, said upper guide locking ducts precisely meeting the locking ducts in the upper extremity of the nail;

(e) inserting bone screws into the upper extremity locking ducts to secure the nail to the bone;

(f) detaching the upper guide and the perforator-guide;

(g) attaching the lower guide to the lower extremity of the nail and drilling holes into the bone using the locking ducts of the lower guide, said lower guide locking ducts precisely meeting the locking ducts of the lower extremity of the nail, and inserting bone screws into the lower extremity locking ducts to secure the nail to the bone; and (h) detaching the lower guide from the nail.

9. A method according to claim 8 wherein (a) the interlocking system further comprises an adapter detachably mounted between the lower extremity of the nail and the lower guide;

(b) in step (g) the lower guide is attached to the lower extremity of the nail by attaching the lower guide to the adapter and the adapter to the lower extremity; and (c) in step (h) the lower guide and the adapter are detached from the nail.

\* \* \* \* \*